US012599550B2

(12) United States Patent
Roll et al.

(10) Patent No.: US 12,599,550 B2
(45) Date of Patent: Apr. 14, 2026

(54) HIGH DOSE AND LOW VOLUME BOTULINUM TOXIN TREATMENT OF FACIAL WRINKLES

(71) Applicant: Merz Pharma GmbH & Co. KGAA, Frankfurt am Main (DE)

(72) Inventors: Susanna Roll, Stadecken-Elsheim (DE); Meik Sladek, Frankfurt am Main (DE); Thorin Geister, Frankfurt am Main (DE); Irena Pulte, Frankfurt am Main (DE); Petra Weissenberger, Frankfurt am Main (DE); Gudrun Klein, Frankfurt am Main (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 508 days.

(21) Appl. No.: 18/007,712

(22) PCT Filed: Jun. 4, 2021

(86) PCT No.: PCT/EP2021/064986
§ 371 (c)(1),
(2) Date: Dec. 1, 2022

(87) PCT Pub. No.: WO2021/245223
PCT Pub. Date: Dec. 9, 2021

(65) Prior Publication Data
US 2023/0329996 A1 Oct. 19, 2023

(30) Foreign Application Priority Data
Jun. 5, 2020 (EP) .................................... 20178574

(51) Int. Cl.
*A61K 8/66* (2006.01)
*A61Q 19/08* (2006.01)

(52) U.S. Cl.
CPC ................ *A61K 8/66* (2013.01); *A61Q 19/08* (2013.01); *A61K 2800/91* (2013.01)

(58) Field of Classification Search
None
See application file for complete search history.

(56) References Cited

U.S. PATENT DOCUMENTS

| | | | |
|---|---|---|---|
| 7,829,525 | B2 | 11/2010 | Frevert |
| 7,879,341 | B2 | 2/2011 | Taylor |
| 8,372,645 | B2 | 2/2013 | Taylor |
| 8,398,998 | B2 | 3/2013 | Bigalke et al. |
| 8,652,489 | B2 | 2/2014 | Taylor |
| 9,050,367 | B2 | 6/2015 | Taylor |
| 9,220,783 | B2 | 12/2015 | Taylor |
| 10,105,421 | B2 | 10/2018 | Taylor |
| 2006/0182767 | A1 | 8/2006 | Borodic |
| 2010/0331259 | A1* | 12/2010 | Haunold ................. A61P 21/00 |
| | | | 514/17.7 |
| 2015/0165003 | A1* | 6/2015 | Jung ....................... A61P 25/24 |
| | | | 424/94.67 |
| 2016/0202245 | A1 | 7/2016 | Brünn |

FOREIGN PATENT DOCUMENTS

| | | |
|---|---|---|
| WO | 2005/007185 A2 | 1/2005 |
| WO | 2006/020208 A2 | 2/2006 |
| WO | 2009/114748 A1 | 9/2009 |
| WO | 2013/049508 A1 | 4/2013 |
| WO | 2014/207109 A1 | 12/2014 |
| WO | 2019113133 A1 | 6/2019 |
| WO | 2021245223 A1 | 12/2021 |

OTHER PUBLICATIONS

Ipsen Biopharmaceuticals, Inc., "DYSPORT (abobotulinumtoxinA) for injection", product label, pp. 1-38. (Year: 2019).*
Carruthers, Alastair, et al. "Dose-ranging study of botulinum toxin type A in the treatment of glabellar rhytids in females" Dermatologic surgery, vol. 31, No. 4, pp. 414-422, Apr. 2005.
Carruthers, Alastair, et al. "Dilution volume of botulinum toxin type A for the treatment of glabellar rhytides: does it matter?" Dermatologic surgery, vol. 33, pp. S97-104, Jan. 2007.
Pearce, L. Bruce, et al. "Measurement of botulinum toxin activity: evaluation of the lethality assay" Toxicology and Applied Pharmacology, vol. 128, No. 1, pp. 69-77, Sep. 1994.
Weisemann, Jasmin, et al. "Generation and characterization of six recombinant botulinum neurotoxins as reference material to serve in an international proficiency test" Toxins, vol. 7, No. 12, pp. 5035-5054, Nov. 2015.
Bertucci, Vince, et al. "DaxibotulinumtoxinA for Injection has a prolonged duration of response in the treatment of glabellar lines: Pooled data from two multicenter, randomized, double-blind, placebo-controlled, phase 3 studies (SAKURA 1 and SAKURA 2)" Journal of American Academy of Dermatology, vol. 82, No. 4, pp. 838-845, Apr. 2020.
Brodsky, Matthew A., et al. "Diffusion of Botulinum Toxins" Tremor and Other Hyperkinetic Movements, Aug. 2012.
Carruthers, Jean, et al. "Consensus Recommendations on the Use of Botulinum Toxin Type A in Facial Aesthetics" Plastic and Reconstructive Surgery, vol. 114, Supplement 6, 1S-22S, Nov. 2004.
Clinical Trial NCT01583478, "Comparison of Escalating Doses of IncobotulinumtoxinA (Xeomin®) in the Treatment of Glabellar Rhytids" Retrieved from https://clinicaltrials.gov/ct2/show/NCT01583478 on Mar. 31, 2023 (10 pages).

(Continued)

*Primary Examiner* — Michelle F. Paguio Frising
(74) *Attorney, Agent, or Firm* — McBee, Moore & Vanik IP, LLC

(57) ABSTRACT

The present invention relates the use of botulinum toxin for the treatment of facial wrinkles, wherein botulinum toxin is administered at high doses (e.g., 50 U to 200 U) using small injection volumes (e.g., 0.05 ml to 0.35 ml). Furthermore, the present invention relates to a method for the treatment of facial wrinkles (e.g., glabellar frown lines) by injecting small volumes of a highly concentrated botulinum toxin solution into a target facial area of a subject.

12 Claims, No Drawings

(56)            References Cited

OTHER PUBLICATIONS

De Almeida, Ada Trindade, et al. "Diffusion characteristics of botulinum neurotoxin products and their clinical significance in cosmetic applications" Journal of Cosmetic and Laser Therapy, vol. 9, Supplemental 1, pp. 17-22, 2007.

De Boulle, Koenraad, et al. "Treating glabellar lines with botulinum toxin type A-hemagglutinin complex: A review of the science, the clinical data, and patient satisfaction" Clinical Interventions in Aging, vol. 5, pp. 101-118, Apr. 2010.

Garcia-Murray, Enrique, et al. "Safety and Efficacy of RT002, an Injectable Botulinum Toxin Type A, for Treating Glabellar Lines: Results of a Phase 1/2, Open-Label, Sequential Dose-Escalation Study" American Society for Dermatologic Surgery, vol. 41, Supplement 1:S47-55, Jan. 2015.

Hexsel, Doris, et al. "Full-Face Injections of Variable Total Doses of Abobotulinum Toxin Type A: A Randomized, Phase IV Clinical Trial of Safety and Efficacy" Journal of Drugs in Dermatology, vol. 12, Issue 12, pp. 1356-1362, Dec. 2013.

Iozzo, Ivano, et al. "Multipoint and multilevel injection technique of botulinum toxin A in facial aesthetics" Journal of Cosmetic Dermatology, vol. 13, No. 2, pp. 135-142, Jun. 2014.

Kerscher, Martina, et al. "IncobotulinumtoxinA: A Highly Purified and Precisely Maiiufactured Botulinum Neurotoxiii Type A" Journal of Drugs in Dermatology, vol. 18, Issue 1, pp. 52-57, Jan. 2019.

Klein, Arnold William. "Complications and Adverse Reactions With the Use of Botulinum Toxin" Disease-a-Month, vol. 48, No. 5, pp. 336-356, May 2002.

Maas, Corey, et al. "Safety and efficacy of escalating doses of incobotulinumtoxina for extended treatment of glabellar frown lines: A randomized double-blind study" Journal of American Academy of Dermatology, vol. 79, No. 3, Supplement 1, AB250, Sep. 2018.

Maas, Corey, et al. "Escalating Doses of Incobotulinumtoxin A for Extended Treatment of Glabellar Frown Lines: Results from a Randomized, Double-Blind Study" International Neurotoxin Association, poster presentation, P6.12, 2019. https://www.neurotoxins.org/toxins/2019/posters/056.pdf.

Ramirez-Castaneda, Juan, et al. "Diffusion, Spread, and Migration of Botulinum Toxin" Movement Disorders, vol. 28, No. 13, pp. 1775-1783, Nov. 2013.

PCT International Search Report for PCT/EP2021/064986, mailed Aug. 24, 2021.

Samizadeh, Souphiyeh, and Koenraad De Boulle. "Botulinum neurotoxin formulations: overcoming the confusion." Clinical, cosmetic and investigational dermatology, (2018), vol. 11: 273-287.

Carruthers, Alastair, and Jean Carruthers. "Prospective, double-blind, randomized, parallel-group, dose-ranging study of botulinum toxin type A in men with glabellar rhytids." Dermatologic surgery, (2005), vol. 31, No. 10: 1297-1303.

Joseph, John H., et al. "Does increasing the dose of abobotulinumtoxina impact the duration of effectiveness for the treatment of moderate to severe glabellar lines ?." Journal of Drugs in Dermatology: JDD, (2016), vol. 15, No. 12: 1544-1549.

Carruthers et al., "DaxibotulinumtoxinA for Injection for the Treatment of Glabellar Lines: Results from Each of Two Multicenter, Randomized, Double-Blind, Placebo-Controlled, Phase 3 Studies (SAKURA 1 and SAKURA 2)," Plast. Reconstr. Surg. 2020, 145(1):45-58.

Carruthers et al., "Injectable DaxibotulinumtoxinA for the Treatment of Glabellar Lines: A Phase 2, Randomized, Dose-Ranging, Double-Blind, Multicenter Comparison With OnabotulinumtoxinA and Placebo," American Society for Dermatologic Surgery, Inc., Wolters Kluwer Health, Inc., Dermatol. Surg., 2017, 43:11, pp. 1321-1331.

Carruthers et al., "Prospective, Double-Blind, Randomized, Parallel-Group, Dose-Ranging Study of Botulinum Toxin Type A in Men with Glabellar Rhytids," Dermatol. Surg. 2005, 31:1297-1303.

Monheit et al., "A Randomized, Double-Blind, Placebo-Controlled Study of Botulinum Toxin Type A for the Treatment of Glabellar Lines: Determination of Optimal Dose", American Society for Dermatologic Surgery, Inc., 33; S51-59 (2007).

Hsu, T.S. Jeffrey, et al. "Effect of Volume and Concentration on the Diffusion of Botulinum Exotoxin A" Archives of Dermatology, vol. 140, No. 11, pp. 1351-1354, Nov. 2004.

Farahvash, M. Reza, and Simin Arad. "Clostridium botulinum type A toxin for the treatment of upper face animation lines: an Iranian experience." Journal of cosmetic dermatology 6, No. 3 (2007): 152-158.

Third Party Opposition in EP Patent Application No. 21728601.2, issued Aug. 26, 2025.

Xeomin® US Food & Drug Administration (FDA) label (revised publication dated May 2019).

Daxxify® US Food & Drug Administration (FDA) label (revised publication dated Sep. 2022).

Frevert, Jürgen. "Pharmaceutical, biological, and clinical properties of botulinum neurotoxin type A products." Drugs in R&D 15, No. 1 (2015): 1-9.

Webpage providing a list of posters presented at Toxins 2019 Conference. Accessed Aug. 15, 2025. https://www.neurotoxins.org/toxins-2019/presented-posters/.

Maas, Corey. "Escalating Doses of Incobotulinumtoxina for Extended Treatment of Glabellar Frown Lines: Safety and Efficacy Results from a Randomized, Double-Blind Study," Toxicon, (2018), vol. 156, pp. S2-S120.

Screenshot of webpage from which D14C was obtained, said webpage confirming this abstract was "Available online Jan. 16, 2019."

Car, Halina, et al. "Botulinum toxin type-A preparations are not the same medications—Basic science (Part 1)." Neurologia i neurochirurgia polska, (2021), vol. 55, No. 2: 133-140.

Ascher, Benjamin, et al. "Liquid formulation of abobotulinumtoxinA exhibits a favorable efficacy and safety profile in moderate to severe glabellar lines: a randomized, double-blind, placebo-and active comparator-controlled trial." Aesthetic Surgery Journal, (2018), vol. 38, No. 2: 183-191.

PCT International Preliminary Report on Patentability for PCT Application No. PCT/EP2021/064986, issued Dec. 6, 2022.

Polacco, Marc A., et al. "A double-blind, randomized clinical trial to determine effects of increasing doses and dose-response relationship of incobotulinumtoxinA in the treatment of glabellar rhytids." Aesthetic Surgery Journal, (2021), vol. 41, No. 6: NP500-NP511.

Kaufman-Janette, Joely, et al. "Botulinum toxin type A for glabellar frown lines: what impact of higher doses on outcomes?." Toxins, (2021), vol. 13, No. 7: 494.

Joseph, John, et al. "AbobotulinumtoxinA for the Treatment of Moderate-to-Severe Glabellar Lines: A Randomized, Dose-Escalating, Double-Blind Study." Journal of Drugs in Dermatology: JDD, (2021), vol. 20, No. 9: 980-987.

Cox, Sue Ellen, et al. "Safety, Pharmacodynamic Response, and Treatment Satisfaction with Onabotulinumtoxina 40 U, 60 U, and 80 U in Subjects with Moderate-to-Severe Dynamic Glabellar Lines," Toxicon, (2020), vol. 190: 514.

Kerscher, Martina, et al. "IncobotulinumtoxinA demonstrates safety and prolonged duration of effect in a dose-ranging study for glabellar lines." Journal of Drugs in Dermatology, (2020), vol. 19, No. 10: 985-991.

Ascher, Benjamin, et al. "Botulinum toxin A in the treatment of glabellar lines: scheduling the next injection." Aesthetic Surgery Journal, (2005), vol. 25, No. 4: 365-375.

Moy, Ronald, et al. "Long-term safety and efficacy of a new botulinum toxin type A in treating glabellar lines." Archives of facial plastic surgery, (2009), vol. 11, No. 2: 77-83.

Joseph, et al. a poster presentation that took place between Jan. 25-29, 2021.

Cohen, Joel L., et al. "An analysis of the long-term safety data of repeat administrations of botulinum neurotoxin type A-ABO for the treatment of glabellar lines." Aesthetic Surgery Journal, (2009), vol. 29, No. 6_Supplement: S43-S49.

Botox® "therapeutic" US Food & Drug Administration (FDA) label, having a revised publication date of Aug. 2011.

(56)                    References Cited

OTHER PUBLICATIONS

Bocouture® UK label SmPC published Dec. 15, 2018.
Webpage obtained directly from the EMC website that outlines the "Changes History" of the SmPC for Bocouture® between Dec. 15, 2018 and Aug. 25, 2021. Accessed Aug. 15, 2025. https://www.medicines.org.uk/emc/product/600/smpc/history.
Bocouture® Czechia label having a revised publication date of Feb. 13, 2020.
Walker, Thomas J., and Steven H. Dayan. "Comparison and overview of currently available neurotoxins." The Journal of clinical and aesthetic dermatology, (2014), vol. 7, No. 2: 31.
Botox® "cosmetic" US Food & Drug Administration (FDA) label (revisesd publication dated Nov. 2019).
Definition of 'devoid' as listed in the Oxford Dictionary. Accessed Nov. 11, 2025. https://www.oxfordlearnersdictionaries.com/definition/english/devoid?q=devoid.
Wu, Yan, et al. "IncobotulinumtoxinA for glabellar frown lines in Chinese subjects: a randomized, double-blind, active-controlled phase-3 study." Plastic and Reconstructive Surgery-Global Open, (2023), vol. 11, No. 5: e4956.
Third Party Opposition in EP Patent Application No. 21728601.2, issued Oct. 7, 2025.

AbbVie News Center. 2018. Allergan Announces Results of Higher Dose Botox® Cosmetic (onabotulinumtoxinA) for the Treatment of Moderate to Severe Glabellar Lines. Sep. 14. Accessed Oct. 1, 2025. https://news.abbvie.com/2018-09-14-Allergan-Announces-Results-of-Higher-Dose-BOTOX-R-Cosmetic-onabotulinumtoxinA-for-the-Treatment-of-Moderate-to-Severe-Glabellar-Lines.
Small, Rebecca. "Botulinum toxin injection for facial wrinkles." American family physician, (2014), vol. 90, No. 3: 168-175.
Lanoue, Julien, et al. "An update on neurotoxin products and administration methods." Cutis, (2016), vol. 98, No. 3: 163-166.
Rappl, Thomas, et al. "Onset and duration of effect of incobotulinumtoxinA, onabotulinumtoxinA, and abobotulinumtoxinA in the treatment of glabellar frown lines: a randomized, double-blind study." Clinical, Cosmetic and Investigational Dermatology, (2013): 211-219.
Tremaine, Anne Marie, and Jerry L. McCullough. "Botulinum toxin type A for the management of glabellar rhytids." Clinical, cosmetic and investigational dermatology, (2010): 15-23.
Nestor, Mark, et al. "Key parameters for the use of abobotulinumtoxinA in aesthetics: onset and duration." Aesthetic surgery journal, (2017), vol. 37, No. suppl_1: S20-S31.

* cited by examiner

HIGH DOSE AND LOW VOLUME BOTULINUM TOXIN TREATMENT OF FACIAL WRINKLES

CROSS-REFERENCE TO RELATED APPLICATIONS

This application is the National Stage entry of International Application No. PCT/EP2021/064986, filed 4 Jun. 2021, which claims priority to European Patent Application No. 20178574.8, filed 5 Jun. 2020.

BACKGROUND

Field

The present invention generally relates to the use of botulinum toxin for the treatment of facial wrinkles, wherein the botulinum toxin is administered at high doses using small injection volumes. In addition, the present invention relates to a method for the treatment of facial wrinkles, such as glabellar frown lines, by injecting a high dose of botulinum toxin in an area of a subject's face using small volumes of a highly concentrated botulinum toxin solution.

Description of Related Art

Botulinum toxin injections to improve the appearance of facial wrinkles have become common in recent years and are now the most popular of all cosmetic procedures worldwide. Botulinum toxin is produced by anaerobic fermentation of the bacterium *Clostridium botulinum*. Several different strains of *C. botulinum* have been identified, which produce eight immunologically distinct serotypes (types A-H).

Serotypes A and B have been developed for human use, with botulinum toxin seroype A preparations being the most widely used worldwide and US FDA approved for aesthetic use. There are currently three leading botulinum toxin type A products on the market: onabotulinumtoxin A (Botox®/Vistabel®, Allergan, Inc., Irvine, CA, USA), abobotulinumtoxin A (Dysport®/Azzalure®, Ipsen, Paris, France), and incobotulinumtoxin A (Xeomin®/Bocouture®, Merz Pharmaceuticals GmbH, Frankfurt Germany).

All serotypes of botulinum toxin are produced by *C. botulinum* in their native form as stable and non-covalent macromolecular protein complexes. These protein complexes consist of the active 150 kDa neurotoxin and non-toxic neurotoxin-associated proteins (NAPs). All 150 kDa neurotoxin serotypes are synthesized as single chain proteins (about 150 kDa) that are proteolytically cleaved into di-chain proteins consisting of a 50 kDa light chain and a 100 kDa heavy chain, connected by a disulfide bond. The botulinum neurotoxin-NAP complexes isolated from *C. botulinum* type A cultures vary in molecular weight (300-900 kDa) depending on the composition of NAPs, which in turn depends on the manufacturing process.

The repetitive contraction and activity of the muscles involved in facial expression is a major factor in the formation of lines and wrinkles, especially in the forehead and around the eye. Botulinum toxin blocks the release of acetylcholine into the synaptic cleft, thus preventing the cholinergic neuromuscular innervation of striated and smooth muscles required for muscle contraction. It therefore can be used to treat all wrinkles that are the result of normal facial movement (dynamic wrinkles). For this purpose, botulinum toxin is administered by targeted injections in the respective muscles to achieve the desired cosmetic effect, e.g. to smoothen out facial wrinkles.

However, along with its intended effects, botulinum toxin may also cause some unwanted effects. For example, as a result of volume and/or dose of injection, injection technique or needle size, the neurotoxin may spread from the original injection site to nearby muscle(s) leading to an undesirable paralyzing effect. Furthermore, botulinum toxin has the potential to induce an immune response, which can lead to the development of neutralizing antibodies that may result in secondary non-responsiveness. While immunogenicity may not be a major issue in aesthetic indications treated with low doses, it may become a concern in subjects receiving high doses, frequent dosing (short treatment intervals), high number of injections, and/or treatment over a prolonged period. Therefore, clinical strategies to reduce or eliminate neutralizing antibody development are warranted and include using the lowest effective dose and prolonging the treatment interval to the longest acceptable interval between injections.

The effects of botulinum toxins are not permanent, but rather reverse over time due to sprouting of nerve terminals and formation of new synaptic contacts. For aesthetic treatments, clinical weakening of the cosmetic effects is typically observed within 3 to 4 months. Therefore, to maintain the desired skin appearance, botulinum toxin needs to be reinjected every 3 to 4 months. The duration of action, and thus the time between two treatments, is an important factor of patient satisfaction with longer treatment intervals being generally desirable. Furthermore, longer treatment intervals reduce the immunogenic risk of neutralizing antibody formation. For these reasons, efforts have been made in the development of modified treatment regimens that may lead to prolonged treatment intervals.

For example, in a previous dose ranging study of botulinum toxin type A with respect to the treatment of glabellar rhytids in females, the efficacy, safety, and duration of effect of four doses of botulinum toxin type A (10 U, 20 U, 30 U and 40 U) were compared. A dose-dependent increase in duration of effect, as well as in the response rate at maximum frown with no increase in adverse events was observed. Statistically significant differences were seen between the 10 U and 40 U dose. However, there were no statistically significant differences between the 20 U, 30 U and 40 U dose groups. The study authors concluded that 20 U is an effective dose for the treatment of glabellar rhytids and that 3 to 4 months is an appropriate inter-treatment interval (Carruthers et al., Dose-Ranging Study of Botulinum Toxin Type A in the Treatment of Glabellar Rhytids in Females, Dermatol. Surg. 2005, 31:414-422).

In a similar study in men, doses of 20 U, 40 U, 60 U and 80 U BoNT/A were administered in the treatment of glabellar rhytids. Overall, there was a dose-dependent increase in both the response rate at maximum frown and the duration of effect. The 40 U, 60 U, and 80 U doses were consistently more effective than the 20 U dose in regard to both the extent and duration of effect (Carruthers A. and Carruthers, J., Prospective, Double-Blind, Randomized, Parallel-Group, Dose-Ranging Study of Botulinum Toxin Type A in Men with Glabellar Rhytids, Dermatol. Surg. 2005, 31:1297-1303).

A Phase II dose-ranging study limited to a single indication (glabellar frown lines) was conducted by Merz in 2006 to 2007 (study MRZ 60201-0527 titled: 'A prospective, randomized, double-blind, placebo-controlled, multicenter trial to determine the optimal dose of NT 201, free of complexing proteins, in the treatment of glabellar frown lines.'). In addition to placebo, the doses tested were 10 U, 20 U, and 30 U of NT 201 (Xeomin®). In this study a dose-dependent increase of responder rate and duration of effect was observed. Despite this, a dose of 20 U was chosen for the two following pivotal GFL studies (0724 and 0741) (see, e.g., Therapeutics Goods Administration (TGA), Aus-PAR Attachment 2, Submission PM-2012-04159-1-1, Extract from the Clinical Evaluation Report for botulinum toxin type A—Xeomin—Merz Australia, 2014).

In a recent open-label trial of 30 subjects with moderate to severe glabellar lines at maximum frown, 120 U abobotulinumtoxinA were injected in 5 equal aliquots into each of 5 injection sites. It was found that 120 U abobotulinumtoxinA were significantly effective in reducing glabellar lines for a longer duration than the dose of 50 U used in FDA Phase Ill randomized, placebo-controlled studies (Joseph et al., Does Increasing the Dose of abobotulinumtoxina Impact the Duration of Effectiveness of the Treatment of Moderate to Severe Glabellar Lines?, J. Drugs Dermatol. 2016, 15(12):1544-1549).

Furthermore, the efficacy and safety of daxibotulinumtoxinA ("DAXI"; Revance Therapeutics, Inc., Newark, CA, USA), a novel botulinum toxin type A formulation, have been evaluated in recent studies relating to the treatment of glabellar frown lines (GFL). The DAXI formulation consists of highly purified daxibotulinumtoxinA (RTT150, a 150-kDa botulinum toxin type A) together with a proprietary stabilizing peptide of 35 amino acids (RTP004), which binds to the neurotoxin with high avidity, and other excipients including polysorbate-20 (a surfactant), buffers, and a sugar.

In a Phase 2 study, subjects with moderate or severe glabellar lines at maximum frown were randomly assigned to 20 U, 40 U, or 60 U daxibotulinumtoxinA, 20 U onabotulinumtoxinA, or placebo. The injection volume per injection point was 0.1 ml. The 40 U and 60 U doses demonstrated a longer duration of effect as compared to 20 U daxibotulinumtoxinA and 20 U onabotulinumtoxinA. The 60 U daxibotulinumtoxinA dose was not further pursued due to increased adverse effects, especially eyelid ptosis, resulting in an unfavorable risk benefit assessment (Carruthers et al., Injectable DaxibotulinumtoxinA for the Treatment of Glabellar Lines: A Phase 2, Randomized, Dose-Ranging, Double-Blind, Multicenter Comparison With OnabotulinumtoxinA and Placebo, Dermatol. Surg. 2017, 43(11): 1321-1331).

Further, in two pivotal Phase Ill studies with 40 U daxibotulinumtoxinA, a prolonged duration of effect was demonstrated. Composite investigator and subject ratings of maximum frown after daxibotulinumtoxinA treatment showed that glabellar line severity of none or mild was maintained for a median of 24.0 weeks (SAKURA 1) and 23.9 weeks (SAKURA 2) (Carruthers et al., DaxibotulinumtoxinA for Injection for the Treatment of Glabellar Lines: Results from Each of Two Multicenter, Randomized, Double-Blind, Placebo-Controlled, Phase 3 Studies (SAKURA 1 and SAKURA 2), Plast. Reconstr. Surg. 2020, 145(1):45-58).

Although investigators have focused primarily on efficacy and duration of action at varying doses, the effect of different dilutions on efficacy and duration of effect have been investigated in a few experimental studies, but with controversial results. Carruthers et al. found that dilution had no significant effect on efficacy or duration of effect. However, an increase in the incidence of adverse effects was observed with higher dilutions (Carruthers et al., Dilution Volume of Botulinum Toxin Type A for the Treatment of Glabellar Rhytides: Does It Matter? Dermatol. Surg. 2007, 33:S97-S104).

Further, Hsu et al. used different dilutions and found that larger volumes resulted in a greater diffusion and a larger affected area. Thus, to treat larger, confluent areas, such as the forehead, a larger volume can be used to achieve more spread. This also means fewer injections, which is important in the pain-averse patients. However, Hsu et al. noted that a greater volume might possibly be accompanied by a decrease in duration and magnitude as well as undesirable spread into neighboring muscles (Hsu et al., Effect of Volume and Concentration on the Diffusion of Botulinum Exotoxin A, Arch. Dermatol. 2004, 140(11):1351-1354).

A longer duration of treatment effect is generally desirable since it offers the possibility to lessen the frequency of retreatment, thereby enhancing patient satisfaction, a key measure of success for aesthetic treatments. Furthermore, this also reduces the risk of neutralizing antibody formation. Against this background, there exists an increasing demand for aesthetic botulinum toxin treatments of the face providing longer lasting results, i.e. a longer period of amelioration of facial wrinkles, while preserving the safety of current treatments.

OBJECT OF THE INVENTION

It is an object of the invention to improve the botulinum toxin treatment of facial wrinkles by providing a longer duration of effect while preserving the safety level of current treatments.

SUMMARY OF THE INVENTION

It has been found that the administration of high doses of botulinum toxin using small injection volumes advantageously provides a prolonged duration of effect, i.e. a longer period of amelioration of facial wrinkles, while maintaining a favourable safety profile. This beneficially allows for the current frequency of administration to be shortened, thereby enhancing patient satisfaction.

Thus, in one aspect, the present invention relates to the use of botulinum toxin for the treatment of facial wrinkles, wherein botulinum toxin is injected in a facial area of a subject at a total dose of 50 U to 200 U and a total volume of 0.05 ml to 0.35 ml to treat said facial wrinkles.

A preferred total dose is 70 U to 125 U and a preferred total volume is 0.15 ml to 0.30 ml. The total dose is usually injected at equal amounts in a number of injection points, for example 3 to 6 injection points. The use of such small total volumes (and volumes per injection point) of a highly concentrated solution of botulinum toxin (i.e. high doses at small volumes) are particularly suitable for the treatment of small muscles, such as horizontal forehead lines (HFL), glabellar frown lines (GFL), and periorbital lines (e.g. crow's feet).

In another aspect, the present invention relates to a method for the treatment of facial wrinkles, the method comprising injecting botulinum toxin in a facial area of a subject at a total dose of 50 U to 200 U, preferably 70 U to 125 U, and a total volume of 0.05 ml to 0.35 ml, preferably 0.15 ml to 0.30 ml, to treat said facial wrinkles.

Preferred embodiments of the use and method of the present invention are set forth in the appended claims.

The present invention may be understood more readily by reference to the following detailed description of the invention and the example included therein.

DETAILED DESCRIPTION OF THE INVENTION

The present invention is based on the finding that the combined use of high doses and low injection volumes of botulinum toxin significantly prolongs the duration of treatment effect, i.e. the amelioration of facial wrinkles, while maintaining a favourable safety profile. As a result, longer treatment intervals can be used which in turn means less injection procedures and less injection-related discomfort. Thus, the high dose, low volume application of botulinum toxin according to the present invention beneficially achieves a very high degree of efficacy which allows for longer treatment intervals, thus enhancing patient satisfaction. Furthermore, the longer treatment intervals decrease the immunogenic risk of neutralizing antibody formation which can lead to secondary treatment failure.

Since the pharmacodynamics of botulinum toxin, e.g. botulinum toxin type A, are not dose-proportional, an increase in dose is not accompanied by a proportional increase in effect. This makes it difficult to predict the effect size following an increase in dose. Extrapolation from already tested doses is not possible. Furthermore, possible side effects, for example side effects caused by toxin spread to adjacent unintended muscles depending on dose and/or volume, can neither be predicted nor foreseen. Thus, whether a given dose range results in a significant prolongation of effect without compromising the safety of the subjects, can only be verified by experimental investigation. The present inventors have carried out respective experimental efforts and found that the combination of high doses and low injection volumes results in sustained duration of effect, a favorable field of effect with no side effects, and completed the present invention.

In a first aspect, the present invention relates to the use of botulinum toxin for the treatment of facial wrinkles, wherein botulinum toxin is injected in a facial area of a subject at a total dose of 50 U to 200 U and a total volume of 0.05 ml to 0.35 ml to treat said facial wrinkles.

Preferably, the total dose of injected botulinum toxin is 50 U to 175 U or 60 U to 150 U or 70 U to 125 U or 75 U to 100 U. The total dose of injected botulinum toxin can preferably also be in a range of 65 U to 95 U or 70 U to 80 U or 72 U to 78 U. The total dose of injected botulinum toxin can also be in the range of 85 U to 125 U or 90 U to 110 U or 95 U to 105 U. Exemplary doses include 50 U, 55 U, 60 U, 65 U, 70 U, 75 U, 80 U, 85 U, 90 U, 95 U, 100 U, 105 U, 110 U, 115 U, 120 U, 125 U, 130 U, 135 U, 140 U, 145 U, 150 U, 155 U, 160 U, 165 U, 170 U, and 175 U. Particularly preferred is a dose range of 70 U to 125 U, in particular if the facial wrinkles to be treated are selected from horizontal forehead lines (HFL), glabellar frown lines (GFL), and periorbital lines (e.g. crow's feet).

As used herein, the dose is expressed in biological units because the used botulinum toxin may contain, for example, variable percentages of inactive toxin that contribute to the overall protein load without contributing to efficacy. Within the context of the present invention, the biological potency of botulinum toxin is determined using the mouse bioassay (MBA). The MBA determines the mean lethal dose (LDso) of toxin/neurotoxin after intraperitoneal injection in mice, i.e. the dose of toxin/neurotoxin capable of killing 50% of a group of mice. On this basis, 1 unit (U) of toxin/neurotoxin, as used herein, is defined as one mouse LD50 (1.0 LD50=1.0 U). The LD50 mouse bioassay is the gold standard among various biological, chemical or immunological detection methods for botulinum toxin and is known to those skilled in the art (see, e.g., Pearce, L. B.; Borodic, G. E.; First, E. R.; MacCallum, R. D. Measurement of botulinum toxin activity: Evaluation of the lethality assay. Toxicol. Appl. Pharmacol. 1994, 128, 69-77).

Another useful method for determining the biological activity of a botulinum neurotoxin is a cell-based assay as it is disclosed, for example, in WO2009/114748, WO 2013/049508 or WO 2014/207109. The activity results obtained with such cell-based assays correspond to the activity values obtained in the mouse i.p. LD50 assay. Activity results obtained for botulinum toxin serotype A formulations like commercially available incobotulinumtoxin A (botulinum toxin serotype A, without complexing proteins; Xeomin®, Merz Pharmaceuticals GmbH) or onabotulinumtoxin A (botulinum toxin serotype A, with complexing proteins; Botox®, Allergan Inc.) can be converted to values for other toxins using conversion rates known to the person skilled in the art. For example, the necessary dose of abobotulinumtoxin A (botulinum toxin serotype A, with complexing proteins; Dysport®, Ipsen Biopharm Limited) can be determined by multiplication of the dose of incobotulinumtoxin A or onabotulinumtoxin A with a factor of 2.5 to 5. The dose for rimabotulinumtoxinB (botulinumtoxin serotype B; Myobloc®, Solstice Neurosciences/US WorldMeds LLC) can be calculated by multiplication of the dose of incobotulinumtoxin A or onabotulinumtoxin A with a factor of 20 to 40.

Preferred total volumes of injected botulinum toxin include 0.10 ml to 0.35 ml or 0.10 ml to 0.30 ml or 0.15 ml to 0.35 ml or 0.15 ml to 0.30 ml. Exemplary total volumes include 0.10 ml, 0.12 ml, 0.14 ml, 0.16 ml, 0.18 ml, 0.20 ml, 0.22 ml, 0.24 ml, 0.26 ml, 0.28 ml, 0.30 ml, 0.32 ml, and 0.35 ml. Further exemplary total volumes include 0.23 ml, 0.25 ml, and 0.27 ml. Particulary preferred is a total volume range of 0.15 ml to 0.35 ml or 0.20 ml to 0.30 ml, in particular if the facial wrinkles to be treated are selected from horizontal forehead lines (HFL), glabellar frown lines (GFL), and periorbital lines (e.g. crow's feet).

Within the context of the present invention, the terms "total dose" and "total volume" refers to the total dose and total volume of botulinum toxin, respectively, generally administered in a treatment session (or "injection session") and typically administered by multiple injections at different injection points, in a single area. A treatment session typically lasts less than one hour, e.g. around 30 minutes. The single area is the facial area of the wrinkles to be treated, e.g. glabellar frown lines. This is, the total dose and total volume generally refer to the dose and volume administered for the treatment of a single type of target wrinkle(s). For example, the treatment of glabellar frown lines, horizontal forehead lines and crow's feet are three different treatment areas and three different target wrinkles.

The concentration of the injected botulinum toxin may, for example, be in a range of from 150 U/ml to 2000 U/ml, preferably from 200 U/ml to 1500 U/ml or 250 U/ml to 1000 U/ml or 300 U/ml to 800 U/ml or 350 U/ml to 600 U/ml. The concentration of the injected botulinum toxin may also be in the range of from 250 U/ml to 500 U/ml or 250 U/ml to 350 U/ml or 350 U/ml to 450 U/ml. These high concentrations of botulinum toxin can for example be obtained by reconstituting lyophilized botulinum toxin A with a suitable volume of diluent, usually sterile saline and particularly sterile unpreserved saline.

Depending on the facial wrinkles to be treated and the corresponding target muscles as well as the individual needs of the patient and the preferences of the treating physician, the botulinum toxin may be injected at 2 to 10 injection points, but is normally injected at 3 to 8 (i.e. at 3, 4, 5, 6, 7 or 8) injection points. Preferably, the number of injection points is 4 to 6, more preferably 5. For the forehead (e.g., horizontal forehead lines (HFL), a suitable number of injection points is 4 to 6, in particular 5. For glabellar frown lines (GFL), the number of injection points may be 4 to 6, preferably 5. For periorbital lines, e.g. crow's feet, 3 to 4 injection points per side are preferably injected. Typically, equal aliquots of botulinum toxin are injected at each injection point. This is, the same volume and dose is normally injected per injection point.

The dose applied per injection point is usually 6 U to 50 U, in particular 8 U to 30 U or 10 U to 25 U. Exemplary doses per injection point include 6 U, 8, U, 10 U, 12 U, 14 U, 16 U, 18 U, 20 U, 22 U, 24 U, 26 U, 28 U, 30 U, 32 U, 34 U, 36 U, 38 U, 40 U, 42 U, 44 U, 46 U, 48 U, and 50 U. Other exemplary doses per injection point include 13 U, 15 U, and 17 U. Preferably, the dose per injection point ranges from 8 U to 30 U, more preferably from 10 U to 25 U and most preferably from 14 U to 22 U or from 14 U to 16 U, in particular if the facial wrinkles to be treated are selected from horizontal forehead lines (HFL), glabellar frown lines (GFL), and periorbital lines (e.g. crow's feet).

The volume injected per injection site may range from 0.01 ml to 0.15 ml, but is normally in the range of 0.02 ml to 0.14 ml. Preferably, the volume per injection site is 0.03 ml to 0.10 ml or 0.04 ml to 0.08 ml or 0.04 ml to 0.06 ml at each site of injection. Exemplary volumes per injection point include 0.02 ml, 0.03 ml, 0.04 ml, 0.05 ml, 0.06 ml, 0.07 ml, 0.08 ml, 0.09 ml, 0.10 ml, 0.11 ml, 0.12 ml, 0.13 ml and 0.14 ml.

In accordance with the present invention, it was found that a small injection volume as described above (e.g., 0.05 mL per injection point and 0.25 mL in total) and a high total dose of injected botulinum toxin (e.g., 70 U to 125 U), provides the desired biological effect of a prolonged duration of wrinkle amelioration. No signs or symptoms of mask-like or frozen face were observed, adding to the high patient satisfaction with the aesthetic outcome. Furthermore, even though the volume injected in accordance with the present invention is small, it can be technically handled and is particularly suitable when targeting small muscles in the face.

In accordance to the present invention, the botulinum neurotoxin may be administered in consecutive treatment cycles. It is understood that a treatment cycle is the time interval between two administrations of the botulinum neurotoxin, i.e. a treatment cycle consists of one administration of the botulinum neurotoxin and a follow-up period until the next botulinum neurotoxin injection is administered. The said administration of botulinum toxin occurs in a treatment session (or "injection session"). The time interval between two consecutive administrations of the botulinum neurotoxin can vary between about 5 and 10 months, in particular between 6 and 9 months. This prolonged treatment interval is enabled by the longer duration of effect achieved by the present invention. For example, for a dose of about 50 U (e.g. 50 U to 59 U), the treatment interval can be 150 days to 210 days (e.g., 170 to 200 days). For a dose of about 75 U (e.g., 60 U to 89 U), the treatment interval can be 180 days to 240 days (e.g. 200 days to 230 days). For a dose of about 100 U (e.g., 90 U to 110 U), the treatment interval can be 210 days to 300 days (e.g., 230 days to 270 days). Further, for a dose (i.e. total dose administered per treatment session) of about 50 U (e.g., 50 U to 59 U), the treatment interval can be from 150 days to 220 days or from 150 days to 210 days (e.g., from 170 days to 220 days or from 170 days to 210 days or from 180 days to 190 days), preferably from 180 days to 200 days. For a dose of about 75 U (e.g., 60 U to 89 U), the treatment interval can be from 180 days to 240 days (e.g., from 180 days to 220 days or from 200 days to 230 days or from 190 days to 220 days), preferably from 200 days to 220 days. For a dose of about 100 U (e.g., 90 U to 110 U), the treatment interval can be from 180 days to 300 days or from 190 days to 260 days or from 210 days to 270 days (e.g., from 200 days to 240 days or from 210 days to 230 days), preferably from 220 days to 240 days.

Moreover, despite the reduced injection volume, the field of effect (i.e. the area showing an effect after toxin injection and in which the muscle will be affected) was found to be large enough to achieve a high responder rate, for example a responder rate of 100% for glabellar frown lines (GFL) (responder: >1-point improvement as assessed by the investigator at maximum frown at day 30). In addition, the observed dose-dependent prolongation of effect was not associated with an increase in the number of unwanted side effects. Without being bound by theory, it is believed that the small injection volumes prevented the toxin from migrating to unintended muscles, thereby avoiding unwanted side effects.

In accordance with the present invention, the botulinum toxin is used in the treatment of facial wrinkles. The treatment of wrinkles is a purely aesthetic application. In other words, within the present invention, botulinum toxin is used for cosmetic purposes.

The term "wrinkles", as used herein, is to be broadly construed to not only include wrinkles, but also lines, rhytids, creases, furrows, and folds. The words "lines", "wrinkles", "rhytids", "creases", and "folds" share similar definition and are therefore often used interchangeably. Within the present invention, "lines" are generally interchangeable with "wrinkles" but may preferably refer to a cutaneous depression that is less deep than a "wrinkle". A "fold" is interchangeable with wrinkles and lines and is preferably a linear depression. A "crease" is interchangeable with wrinkles, lines and folds. It preferably refers to a mild form of wrinkles and may describe the specific wrinkle in certain locations. A "rhytid", as used herein, has essentially the same meaning of wrinkle. However, a "rhytid" preferably refers to a skin structure that is formed by irregular aggregation of lines. A "furrow" is a deep fold or deep line in the skin.

The facial wrinkles treated in accordance with the present invention are not particularly limited and may include horizontal forehead lines, glabellar frown lines, periorbital lines, Crow's feet, bunny lines (i.e. downward radiating lines on the sides of nose), nasolabial folds, upper radial lip lines, lower radial lip lines, corner of the mouth lines, marionette lines, perioral lip lines, oral commissures, labiomental crease and cobblestone chin, preferably horizontal forehead lines, glabellar frown lines and periorbital lines (e.g. Crow's feet). The wrinkles that are preferably treated in accordance with the present invention are selected from horizontal forehead lines (HFL), glabellar frown lines (GFL) and periorbital lines (e.g. crow's feet), and are most preferably glabellar frown lines (GFL).

In order to treat the above-mentioned facial wrinkles, botulinum toxin is usually administered by intramuscular injection to the following muscles: frontalis muscle (horizontal forehead lines), procerus and corrugator muscles (glabellar frown lines), lateral orbicularis oculi muscle (Crow's feet/periorbital lines), nasalis, procerus for transverse nasal muscles (bunny lines), levator labii superioris alaeque nasi muscles (nasolabial folds), orbicularis oris muscles (upper radial lip lines), orbicularis oris muscles (lower radial lip lines), depressor anguli oris muscles (corner of the mouth lines), depressor anguli oris muscles (marionette lines), orbicularis oris, depressor anguli oris, and mentalis muscles (perioral lip lines), depressor anguli oris muscles (oral commissures), depressor anguli oris muscles (labiomental crease), and mentalis muscles (cobblestone chin).

The subject to be treated is not particularly limited other than by having facial wrinkles to be treated. For example, the subject may be a subject with either moderate and severe or (only) severe glabellar frown lines, wherein the severity of the glabellar frown lines is assessed by investigator using the Facial Wrinkle Scale (FWS) at maximum frown. Further, the subject may be (i) a female subject, (ii) a male or female subject of 20 to 80, 30 to 70, or 40 to 60, years of age, (iii) a female subject with either moderate and severe or only severe glabellar frown lines, wherein the severity of the glabellar frown lines is assessed by investigator using the Facial Wrinkle Scale (FWS) at maximum frown.

Moreover, since the use of botulinum toxin according to the present invention may also be used in a prophylactic manner, e.g. for the treatment of subjects (male or female), who have none, or none or mild, glabellar frown lines, wherein the severity of the glabellar frown lines is assessed by investigator using the Facial Wrinkle Scale (FWS) at maximum frown, another subject group of interest are subjects of 20 to 40 or 25 to 35 years of age.

In accordance with a preferred embodiment of the present invention, the botulinum toxin is used in the treatment of horizontal forehead lines (HFL), glabellar frown lines (GFL) or periorbital lines (e.g. crow's feet), preferably in the treatment of glabellar frown lines (GFL), wherein the botulinum toxin is injected (i) at a total dose of 60 U to 130 U and in a total volume of 0.15 ml to 0.35 ml or (ii) at a total dose of 65 U to 110 U and in a total volume of 0.15 ml to 0.30 ml or (iii) at a total dose of 65 U to 90 U and in a total volume of 0.15 ml to 0.30 ml or (iv) at a total dose of 65 U to 90 U and in a total volume of 0.10 ml to 0.25 ml or (v) at a total dose of 80 U to 120 U and in a total volume of 0.15 ml to 0.35 ml or (vi) at a total dose of 80 U to 120 U and in a total volume of 0.15 ml to 0.30 ml or (vii) at a total dose of 72 U to 78 U (e.g. 75 U) in a total volume of 0.25 ml or (vii) at a total dose of 90 U to 110 U (e.g. 100 U) and in a total volume of 0.25 ml, and wherein the botulinum toxin is preferably injected at 3, 4, 5 or 6, more preferably 4 or 5, intramuscular injection points. Moreover, in the preferred embodiment described in this paragraph, the botulinum toxin is preferably of serotype A and is especially the (pure) neurotoxic component of serotype A (e.g., Xeomin®). Furthermore, the subjects to be treated are as defined herein above.

In accordance with another preferred embodiment of the present invention, the botulinum toxin is used in the treatment of moderate or severe glabellar frown lines (GFL) or in the treatment of severe glabellar frown lines (GFL), based on investigator ratings using the Facial Wrinkle Scale (FWS) at maximum frown, wherein the botulinum toxin is injected (i) at a total dose of 60 U to 130 U and in a total volume of 0.15 ml to 0.35 ml or (ii) at a total dose of 65 U to 110 U and in a total volume of 0.15 ml to 0.30 ml or (iii) at a total dose of 65 U to 90 U and in a total volume of 0.15 ml to 0.30 ml or (iv) at a total dose of 65 U to 90 U and in a total volume of 0.10 ml to 0.25 ml or (v) at a total dose of 80 U to 120 U and in a total volume of 0.15 ml to 0.35 ml or (vi) at a total dose of 80 U to 120 U and in a total volume of 0.15 ml to 0.30 ml or (vii) at a total dose of 72 U to 78 U (e.g. 75 U) in a total volume of 0.25 ml or (vii) at a total dose of 90 U to 110 U (e.g. 100 U) and in a total volume of 0.25 ml, and wherein the botulinum toxin is preferably injected at 3, 4, 5 or 6, more preferably 4 or 5, intramuscular injection points. Moreover, in the preferred embodiment described in this paragraph, the botulinum toxin is preferably of serotype A and is especially the (pure) neurotoxic component of serotype A (e.g., Xeomin®). Furthermore, the subjects to be treated are as defined herein above.

For the treatment of glabellar frown lines, the botulinum toxin is usually injected at 4 to 6, preferably 5, intramuscular injection points, preferably into the procerus and corrugator muscles, in particular at two sites in each corrugator muscle and one site in the procerus muscle, for a total of 0.20 to 0.30 ml. Specifically, one injection may be given in the procerus muscle at the crossing of two lines that connect the medial part of the eyebrow and the contralateral caruncle. One injection on each side may be given in the medial (inner) part of the corrugator muscle at least 1 cm above the bony orbital rim on an imaginary line drawn vertically from the caruncle. One injection on each side may be given laterally from the above-mentioned site in the middle part of the corrugator muscle at least 1 cm above the bony orbital rim on an imaginary line drawn vertically from the midpupillary line.

In accordance with the present invention, the botulinum neurotoxin may also be administered together with a dermal filler, either simultaneously or consecutively. In particular, in the treatment of perioral lip lines (orbicularis oris, depressor anguli oris, and mentalis muscles), botulinum toxin may be administered in conjunction with dermal fillers. The dermal filler is preferably a hyaluronic acid-based dermal filler, more preferably a crosslinked hyaluronic acid-based dermal filler.

The botulinum toxin used within the present invention may be a botulinum toxin complex or the neurotoxic component of a botulinum neurotoxin complex. Said neurotoxic component is devoid of any other protein component of the *Clostridium botulinum* neurotoxin complex. Preferably, as mentioned above, the botulinum toxin (i.e. the toxin complex or the pure neurotoxic component) is of serotype A.

More specifically, the term "botulinum toxin", as used herein, includes the 150 kDa neurotoxin itself, i.e. the pure neurotoxin devoid of any NAPs (also referred to herein as "neurotoxic component" or "pure neurotoxic component"), and complexes of the 150 kDa neurotoxin and neurotoxin-associated complexing proteins (NAPs) (referred to herein as "complex" or "toxin complex"). The 150 kDa neurotoxin is the active protein that ultimately inhibits acetylcholine release. NAPs are not pharmacologically active on nerve terminals and typically consist of several hemagglutinins (HA) and a single non-toxic non-hemagglutinin (NTNH).

The full-length neurotoxin type A has a theoretical molecular weight of 150.3 kDa, while the neurotoxins of other serotypes varies from 144.7 kDa (botulinum toxin type E) to 152.9 kDa (botulinum toxin type B) (see Weisemann et al., Toxins 2015, 7(12), 5035-5054). Despite these molecular weight variations, the term "150 kDa neurotoxin", as used herein, is intended to refer to the active neurotoxin (neurotoxic component) of all serotypes, unless otherwise stated. The pure 150 kDa neurotoxin of serotype A without any complexing proteins (NAPs) is contained in the commercial product incobotulinumtoxin A (Xeomin/Bocouture®, Merz Pharmaceuticals GmbH, Frankfurt Germany).

The term "toxin complex", as used herein, is preferably a high-molecular complex of the neurotoxic component and a set of NAPs selected from the 900 kDa, 500 kDa, and/or 300 kDa *C. botulinum* type A toxin complexes. The 900 kDa complex is included in onabotulinumtoxin A (Botox®/Vistabel®, Allergan, Inc., Irvine, CA, USA). Another example of a toxin complex is abobotulinumtoxin A (Dysport®, Azzalure®, Ipsen, Paris, France).

In accordance with the present invention, the botulinum toxin (i.e. the neurotoxic component or toxin complex) may be of serotype A, B, C1, D, E, F or G. Due to its longer lasting effects compared to the other serotypes, botulinum toxin type A is preferably used herein. Furthermore, within the framework of the present invention, the term "botulinum toxin" may refer to a natural neurotoxin obtainable from the bacteria *Clostridium botulinum* or to a botulinum toxin obtainable from alternative sources, including from recombinant technologies or from genetic or chemical modification.

Generally, the botulinum toxin used within the present invention is present in the form of a liquid composition. For preparing a composition comprising a botulinum toxin the neurotoxin can be formulated by various techniques dependent on the desired application purposes which are known in the art. The botulinum toxin used within the present invention is preferably an aqueous solution, more preferably a saline solution or a physiological saline solution, and most preferably a phosphate buffered physiological saline solution. The aqueous solution may additionally comprise one or more pharmaceutically acceptable substances. Suitable pharmaceutically acceptable substances comprise those well known in the art, see, e.g., Remington's Pharmaceutical Sciences, Mack Publishing Company, Easton, Pennsylvania.

In particular, the aqueous botulinum toxin solution or composition may include other carriers or non-toxic, non-therapeutic, non-immunogenic stabilizers and the like. Thus, the aqueous botulinum toxin composition may contain glycerol, protein stabilizers (HSA) or non-protein stabilizers such as polyvinyl pyrrolidone (PVP), hyaluronic acid or free amino acids, e.g. like methionine or histidine. In an aspect, it can be free of amino acids. In an aspect it may be free of stabilizing peptides (e.g., consisting of 5 to 50 amino acids, 10 to 40 amino acids or 15 to 30 amino acids). In an aspect, suitable non-proteinaceous stabilizers are disclosed in WO 2005/007185 or WO 2006/020208. The botulinum toxin composition can also include non-ionic or ionic surfactant, e.g. like polysorbate or poloxamer. A suitable formulation for HSA-stabilized formulation comprising a botulinum toxin according to the present invention is for example disclosed in U.S. Pat. No. 8,398,998 B2.

Preferably, the botulinum toxin used within the present invention is present in the form of an aqueous solution comprising sodium chloride (NaCl), more preferably in the form of a physiological saline solution (i.e. a solution including sodium chloride in physiological concentration, e.g., about 9 g/l NaCl), wherein the aqueous botulinum toxin solution comprises (i) no other excipient (except NaCl), (ii) human serum albumin (HSA) and a sugar, in particular a monosaccharide or a disaccharide, (iii) human serum albumin (HSA) and lactose, (iv) human serum albumin (HSA) and sucrose, (v) a monosaccharide and/or a disaccharide (e.g. lactose and/or sucrose), (vi) no buffer, (vii) no single amino acids, (viii) no human serum albumin (HSA), sodium chloride and lactose or no HSA, sodium chloride and sucrose, or (ix) no HSA and sodium chloride, or any combination of (i) to (ix).

In another aspect, the present invention relates to a method for the treatment of facial wrinkles, the method comprising injecting botulinum toxin in a facial area of a subject at a total dose of 50 U to 200 U and a total volume of 0.05 ml to 0.35 ml to treat said facial wrinkles.

This method of treatment is used for purely aesthetic purposes, i.e. the treatment of facial wrinkles, and is thus a cosmetic method. The botulinum toxin is intramuscularly injected using, e.g., a 30 G, 32 G or 33 G needle and, e.g. a 0.3 mL, 0.5 mL or 1 mL syringe, depending on the volume needed.

The prolonged duration of effect allows for less frequent administration of botulinum toxin. For example, botulinum neurotoxin may be repeatedly administered at an interval between a first administration and a second administration, or between a second or further administration and another administration following said second or further administration (i.e. between consecutive administrations of the botulinum toxin) of between about 5 and 10 months, especially between about 6 and 9 months. For example, for a total dose of about 50 U (e.g., 50 U to 59 U), the treatment interval may be 150 days to 200 days (e.g., 170 to 190 days). For a total dose of about 75 U (e.g., 60 U to 89 U), the treatment interval may be 180 days to 240 days (e.g., 200 days to 230 days). For a dose of about 100 U (e.g., 90 U to 110 U), the treatment interval may be 210 days to 270 days (e.g., 230 days to 260 days). Further, for a total dose of about 50 U (e.g., 50 U to 59 U), the treatment interval may be from 150 days to 220 days or from 150 days to 210 days (e.g., from 170 days to 220 days or from 170 days to 210 days or from 180 days to 190 days), preferably from 180 days to 200 days. For a total dose of about 75 U (e.g., 60 U to 89 U), the treatment interval may be from 180 days to 240 days (e.g., from 180 days to 220 days orfrom 200 days to 230 days or from 190 days to 220 days), preferably from 200 days to 220 days. For a dose of about 100 U (e.g., 90 U to 110 U), the treatment interval may be from 180 days to 300 days or from 190 days to 260 days or from 210 days to 270 days (e.g., from 200 days to 240 days or from 210 days to 230 days), preferably from 220 days to 240 days).

The second aspect of the present invention relating to a cosmetic method of treating facial wrinkles, is closely related to the first aspect of the invention described herein above. Thus, all definitions and explanations provided herein with respect to the first aspect relating the cosmetic use of botulinum toxin equally apply to the second aspect directed to the cosmetic method of treatment.

EXAMPLES

Example 1

Interim Analysis

This example relates to an interim analysis of a prospective, randomized, double-blind, multicentre study. The aim of the study is to investigate the safety and duration of effect of different NT 201 dose groups following the treatment of glabellar frown lines (GFL).

A total of 151 randomized subjects (12.6% male, 87.4% female) of 22 to 76 years with a mean age of 48.9 years were enrolled in the prospective, randomized, double-blind, multicentre study. As per Investigator assessment, 15.3% of the subjects had Grade 2 (Moderate) GFL and 84.7% of the subjects had Grade 3 (Severe) GFL at baseline.

The severity grade of GFL was assessed by the investigator at maximum frown using the 4-point investigator's Facial Wrinkle Scale (investigator's FWS) following treatment compared to the baseline assessment. A photo guide comprising sample photos of each of the four grades was provided to investigators to support their rating by FWS together with descriptors for the four severity grades (see Table 1).

TABLE 1

| Investigator's Facial Wrinkle Scale (Investigator FWS) | | |
| --- | --- | --- |
| Grade | Severity of GFL at maximum frown | Descriptor |
| 0 | None | No muscle action at all |
| 1 | Mild | Some even slight muscle action possible |
| 2 | Moderate | Moderately strong muscle action possible |
| 3 | Severe | Strong muscle action possible which may cause local pallor |

GFL severity was also evaluated by the subjects at maximum frown using the 4-point subject's Facial Wrinkle Scale (subject's FWS). Likewise, a photo guide was provided to the subjects for self-assessment of GFL at maximum frown together with descriptors for the four severity grades (see Table 2)

TABLE 2

| Subject's Facial Wrinkle Scale (subject's FWS) | | |
| --- | --- | --- |
| Grade | Severity of GFL at maximum frown | Descriptor |
| 0 | None | No muscle action at all |
| 1 | Mild | Some even slight muscle action possible (i.e. visible furrows) |
| 2 | Moderate | Moderately strong muscle action possible (i.e. visible muscle bulges) |
| 3 | Severe | Strong muscle action possible which may cause local pallor |

Subjects were randomly assigned to three groups, 20 U NT 201 (N=30), 50 U NT 201 (N=60), and 75 U NT 201 (N=61). All treatments consisted of five 0.05 mL injections, two in each corrugator muscle and one in the procerus muscle for a total of 0.25 mL. In order to inject a total dose of 20 U, 50 U and 75 U, a 200 U vial of NT 201 was reconstituted using varying volumes of sterile unpreserved saline (see Table 3).

TABLE 3

| Reconstitution table | | | | |
| --- | --- | --- | --- | --- |
| | Total Dose 20 U | Total Dose 50 U | Total Dose 75 U | Total Dose 100 U* |
| Dose vial | 200 U | 200 U | 200 U | 200 U |
| Reconstitution volume | 2.5 mL | 1 mL | 0.67 mL | 0.5 mL |
| Number of injection points | 5 | 5 | 5 | 5 |
| Total volume injected | 0.25 mL | 0.25 mL | 0.25 mL | 0.25 ml |
| Volume per injection point | 0.05 mL | 0.05 mL | 0.05 mL | 0.05 mL |
| Dose per injection point | 4 U | 10 U | 15 U | 20 U |

*The 100 U group was analyzed in the final analysis (see Example 2 below).

Subjects were evaluated at eight (8) days following treatment, thirty (30) days after treatment and then every 30 days. As a primary outcome measure (primary efficacy variable), the median duration of effect (medium duration of response, time between treatment for an at least 1-point improvement in investigator's FWS at maximum frown to relapse to baseline values) was estimated. Furthermore, as secondary efficacy variables, the median duration of effect, wherein effect is defined by (a) a score of none (0) or mild (1) or (b) a 2-point improvement from baseline, was assessed by the investigator using the investigator's FWS.

In addition, the proportion (percentage) of subjects at day 180 rated to have a GFL severity of none (0) or mild (1) according to the investigator's FWS as well as the patient's FWS was assessed as a secondary outcome measure (secondary efficacy variable). Other secondary efficacy variables were the percentage of subjects at day 180 with at least a 1-point improvement or the percentage of subjects at day 180 with at least a 2-point improvement from baseline as assessed using the investigator's FWS as well as the patient's FWS. In addition, as another efficacy variable, investigators and subjects evaluated the global aesthetic improvement at each postbaseline visit using the Global Aesthetic Improvement Scale (GAIS), with the following rating score ranging from −3 to 3: very much worse (−3), much worse (−2), worse (−1), no change (0), improved (1), much improved (2), and very much improved (3).

The results of median duration of effect are shown in Table 4.

TABLE 4

| Efficacy variable | NT 201 | | |
| --- | --- | --- | --- |
| (primary/secondary endpoints) | 20 U | 50 U | 75 U |
| Primary efficacy variable | | | |
| median time to relapse to baseline status | 177 d | 185 d | 210 d |
| Secondary efficacy variables | | | |
| Median duration of effect-"none (0) or mild (1)" assessed by investigator's | 112 d | 121 d | 129 d |
| Median duration of effect-"2-point improvement" | 97 d | 118 d | 122 d |

The results of Response rates based on FWS at day 180 are shown in Table 5, and the patient satisfaction using the Global Aesthetic Improvement Scale (GAIS) at day 180 is shown in Table 6.

TABLE 5

| Response rates based on FWS at day 180 (secondary efficacy variables) | | | |
| --- | --- | --- | --- |
| Efficacy variable | NT 201 | | |
| (secondary endpoints) | 20 U | 50 U | 75 U |
| At least 1-point improved | | | |
| by investigator's FWS at maximum frown | 27% | 43% | 53% |
| by subject's FWS at maximum frown | 37% | 37% | 51% |
| "None (0) or mild (1)" | | | |
| by investigator's FWS at maximum frown | 7% | 10% | 16% |
| by subject's FWS at maximum frown | 7% | 10% | 18% |
| At least 2-points improved | | | |
| by investigator's FWS at maximum frown | 7% | 8% | 10% |
| by subject's FWS at maximum frown | 0% | 8% | 15% |

TABLE 6

| Global Aesthetic Improvement Scale (GAIS) at day 180 | | | |
| --- | --- | --- | --- |
| Parameter | NT 201 | | |
| (secondary endpoints) | 20 U | 50 U | 75 U |
| GAIS at least improved | | | |
| by investigator | 39% | 49% | 67% |
| by subject | 36% | 38% | 53% |

The above results demonstrate high responder rates across all dose groups and a dose dependent prolongation of effect. It could be demonstrated that in spite of the reduced injection volume the field of effect was large enough to achieve a responder rate of 100% at day 30 after injection (responder 1-point improvement at max. frown as assessed by the investigator) across all dose groups with a sustained duration of effect.

The incidence of adverse events was comparable to those as known from pivotal Phase Ill studies in the indication GFL. All doses were well tolerated, and the safety profile is consistent with the known safety profile of the approved dose of 20 U NT 201. No new safety concerns were detected. Specifically, no serious TEAEs (treatment-emergent adverse events) occurred. In particular, eyelid ptosis (N=2 of 151) was as low as 1.3%, and no other TEAESIs (treatment-emergent adverse events of special interest) related to treatment occurred.

Furthermore, although within the community of physicians higher doses are frequently associated with frozen face and an increase in adverse events, no signs of frozen face were observed in the present study. Subjects as well as investigators were very satisfied with aesthetic outcome and the long-lasting effect. Overall, the results show that the use of high doses of botulinum toxin concentrated in small injection volumes is very effective, long-lasting, well-tolerated, and safe.

Example 2

Final Analysis

This example relates to the final analysis of the prospective, randomized, double-blind, multicentre study described in Example 1 to investigate the safety and duration of effect of different NT 201 dose groups following the treatment of glabellar frown lines (GFL). The final analysis includes, inter alia, data for a fourth group of patients which were treated with 100 U NT 201 and for 31 additional subjects in the 20 U NT 201 group.

A total of 241 randomized subjects (13.7% male, 86.3% female) of 22 to 76 years with a mean age of 49.4 years were enrolled in the prospective, randomized, double-blind, multicentre study. As per Investigator assessment, 14.1% of the subjects had a severity Grade 2 (Moderate) GFL and 85.9% of the subjects had a severity Grade 3 (Severe) GFL on the Facial Wrinkle Scale at baseline.

The severity grade of GFL was assessed by the investigator at maximum frown using the 4-point investigator's Facial Wrinkle Scale (investigator's FWS) following treatment. A photo guide comprising sample photos of each of the four grades was provided to investigators to support their rating by FWS together with descriptors for the four severity grades (see Table 1).

TABLE 1

| Investigator's Facial Wrinkle Scale (Investigator FWS) | | |
| --- | --- | --- |
| Grade | Severity of GFL at maximum frown | Descriptor |
| 0 | None | No muscle action at all |
| 1 | Mild | Some even slight muscle action possible |
| 2 | Moderate | Moderately strong muscle action possible |
| 3 | Severe | Strong muscle action possible which may cause local pallor |

GFL severity was also assessed by the subjects at maximum frown using the 4-point subject's Facial Wrinkle Scale (subject's FWS). Likewise, a photo guide was provided to the subjects for self-assessment of GFL at maximum frown together with descriptors for the four severity grades (see Table 2)

TABLE 2

| Subject's Facial Wrinkle Scale (subject's FWS) | | |
| --- | --- | --- |
| Grade | Severity of GFL at maximum frown | Descriptor |
| 0 | None | No muscle action at all |
| 1 | Mild | Some even slight muscle action possible (i.e. visible furrows) |
| 2 | Moderate | Moderately strong muscle action possible (i.e. visible muscle bulges) |
| 3 | Severe | Strong muscle action possible which may cause local pallor |

Subjects were randomly assigned to four groups, 20 U NT 201 (N=61), 50 U NT 201 (N=60), 75 U NT 201 (N=61), and 100 U NT 201 (N=59). All treatments consisted of five 0.05 mL injections per injection point, two injections in each corrugator muscle and one injection in the procerus muscle for a total of 0.25 mL. In order to inject a total dose of 20 U, 50 U, 75 U, and 100 U, a 200 U vial of NT 201 was reconstituted using varying volumes of sterile unpreserved saline (see Table 3).

TABLE 3

| Reconstitution table | | | | |
| --- | --- | --- | --- | --- |
| | Total Dose 20 U | Total Dose 50 U | Total Dose 75 U | Total Dose 100 U |
| Dose vial | 200 U | 200 U | 200 U | 200 U |
| Reconstitution volume | 2.5 mL | 1 mL | 0.67 mL | 0.5 mL |
| Number of injection points | 5 | 5 | 5 | 5 |
| Total volume injected | 0.25 mL | 0.25 mL | 0.25 mL | 0.25 ml |
| Volume per injection point | 0.05 mL | 0.05 mL | 0.05 mL | 0.05 mL |
| Dose per injection point | 4 U | 10 U | 15 U | 20 U |

Subjects were evaluated at eight (8) days following treatment, thirty (30) days after treatment and then every 30 days. As a primary outcome measure (primary efficacy variable), the median duration of effect (medium duration of response, time between treatment for an at least 1-point improvement on investigator's FWS at maximum frown to relapse to baseline values) was estimated. Furthermore, as secondary efficacy variables, the median duration of effect was evaluated, wherein effect is defined by (a) a score of none (0) or mild (1) or (b) a 2-point improvement from baseline, as assessed by the investigator using the investigator's FWS.

In addition, the proportion (percentage) of subjects at day 180 with a GFL severity of none (0) or mild (1) at maximum frown as assessed by the investigator's rating on the FWS as well as the patient's rating on FWS was assessed as a secondary outcome measure (secondary efficacy variable). Other secondary efficacy variables were the percentage of subjects at day 180 with an at least 1-point improvement from baseline as assessed by the investigator using the investigator's FWS as well as by the patient using the patient's FWS. In addition, as another efficacy variable, investigators and subjects evaluated the global aesthetic improvement at each postbaseline visit using the Global Aesthetic Improvement Scale (GAIS), with the following rating score ranging from −3 to 3: very much worse (−3), much worse (−2), worse (−1), no change (0), improved (1), much improved (2), and very much improved (3).

The results of median duration of effect are shown in Table 4.

TABLE 4

| Median duration of effect | | | | |
|---|---|---|---|---|
| Efficacy variable | NT 201 | | | |
| (primary/secondary endpoints) | 20 U | 50 U | 75 U | 100 U |
| Primary efficacy variable | | | | |
| Median time to relapse to baseline status | 175 d | 185 d | 210 d | 215 d |
| Secondary efficacy variables | | | | |
| Median duration of effect-"none (0) or mild (1)" assessed by investigator's | 113 d | 121 d | 129 d | 148 d |
| Median duration of effect-"2-point improvement" | 96 d | 118 d | 122 d | 145 d |

The results of response rates based on FWS at day 180 are shown in Table 5., and the response rates based on FWS at day 240 (only for "at least 1-point improved" and "none (0) or mild (1)") are shown in Table 6.

TABLE 5

| Response rates based on FWS at day 180 (secondary efficacy variables) | | | | |
|---|---|---|---|---|
| Efficacy variable | NT 201 | | | |
| (secondary endpoints) | 20 U | 50 U | 75 U | 100 U |
| At least 1-point improved | | | | |
| by investigator's FWS at maximum frown | 33% | 43% | 53% | 53% |
| by subject's FWS at maximum frown | 38% | 37% | 53% | 46% |
| "None (0) or mild (1)" | | | | |
| by investigator's FWS at maximum frown | 8% | 8% | 16% | 19% |
| by subject's FWS at maximum frown | 7% | 10% | 20% | 17% |
| by investigator's FWS at maximum frown | 7% | 7% | 10% | 14% |
| by subject's FWS at maximum frown | 3% | 8% | 15% | 14% |

At least 2-points improved

TABLE 6

| Response rates based on FWS at day 240 (secondary efficacy variables) | | | | |
|---|---|---|---|---|
| Efficacy variable | NT 201 | | | |
| (secondary endpoints) | 20 U | 50 U | 75 U | 100 U |
| At least 1-point improved | | | | |
| by investigator's FWS at maximum frown | 15% | 5% | 13% | 24% |
| by subject's FWS at maximum frown | 7% | 8% | 8% | 24% |
| "None (0) or mild (1)" | | | | |
| by investigator's FWS at maximum frown | 5% | n.a. | 5% | 7% |
| by subject's FWS at maximum frown | 2% | 2% | 2% | 9% |

The investigator's and patient's assessment of overall improvement on the glabella lines using the Global Aesthetic Improvement Scale (GAIS) at day 180 is shown in Table 7.

TABLE 7

| Global Aesthetic Improvement Scale (GAIS) at day 180 | | | | |
|---|---|---|---|---|
| Parameter | NT 201 | | | |
| (secondary endpoints) | 20 U | 50 U | 75 U | 100 |
| GAIS at least improved | | | | |
| by investigator | 42% | 49% | 67% | 75% |
| by subject | 35% | 38% | 53% | 63% |

The above results demonstrate high response rates (responder rates) across all dose groups and a dose dependent prolongation of effect. It could also be demonstrated (results not shown) that in spite of the reduced injection volume the field of effect was large enough to achieve a responder rate of 100% at day 30 after injection (responder 1-point improvement at max. frown as assessed by the investigator) across all dose groups with a sustained duration of effect.

The incidence of adverse events was comparable to those as known from pivotal Phase III studies in the indication GFL. No dose dependent increase in the incidence of overall treatment emergent adverse events or related treatment emergent adverse events was observed. All doses were well tolerated, and the safety profile is consistent with the known safety profile of the approved dose of 20 U NT 201. No new safety concerns were detected. Specifically, no serious TEAEs (treatment-emergent adverse events) occurred. In particular, the incidence of eyelid ptosis (N=4 of 241) was as low as 1.7%, and no other TEAESIs (treatment-emergent adverse events of special interest) related to treatment occurred.

Furthermore, although within the community of physicians higher doses are frequently associated with frozen face and an increase in adverse events, no signs of an unnatural look or frozen face were observed in the present study using doses up to 100 U NT 201. Subjects as well as investigators were very satisfied with the aesthetic outcome and the long-lasting effect. Overall, the results show that the use of high doses of botulinum toxin concentrated in small injection volumes is very effective, long-lasting, well-tolerated, and safe.

19

The invention claimed is:

1. A method of treating facial wrinkles comprising injecting botulinum toxin in a facial area of a subject at a total dose of 50 U to 200 U and a total volume of 0.05 ml to 0.35 ml to treat said facial wrinkles, wherein the botulinum toxin is the neurotoxic component of botulinum toxin serotype A.

2. The method of claim 1, wherein the botulinum toxin is injected at a total dose of 50 U to 175 U or 60 U to 150 U or 70 U to 125 U or 75 U to 100 U.

3. The method of claim 1, wherein the botulinum toxin is injected in a total volume of 0.10 ml to 0.35 ml or 0.10 ml to 0.30 ml or 0.15 ml to 0.35 ml or 0.15 ml to 0.30 ml.

4. The method of claim 1, wherein the botulinum toxin is injected at a concentration of 150 U/ml to 2000 U/ml or 200 U/ml to 1500 U/ml or 250 U/ml to 1000 U/ml or 300 U/ml to 800 U/ml or 350 U/ml to 600 U/ml.

5. The method of claim 1, wherein the botulinum toxin is injected at 3 to 8 injection points and/or wherein the botulinum toxin is injected at a dose of 6 U to 50 U at each injection point.

6. The method of claim 5, wherein the botulinum toxin is injected in a volume of 0.02 ml to 0.14 ml or 0.03 ml to 0.10 ml or 0.04 ml to 0.06 ml at each site of injection.

7. The method of claim 1, wherein the botulinum toxin is used in the treatment of horizontal forehead lines, glabellar frown lines, periorbitallines, Crow's feet, bunny lines, nasolabial folds, upper radiallip lines, lower radiallip lines, corner of the mouth lines, marionette lines, periorallip lines, oral commissures, labiomental crease and cobblestone chin, optionally horizontal forehead lines, glabellar frown lines, and periorbitallines including Crow's feet.

8. The method of claim 1, wherein the subject is a subject with moderate or severe glabellar frown lines, or severe glabellar frown lines, based on assessment by investigator using the Facial Wrinkle Scale (FWS) at maximum frown.

9. The method of claim 1, wherein the subject is a female subject.

10. The method of claim 1, wherein the botulinum toxin is used in the treatment of glabellar frown lines, and wherein the botulinum toxin is injected at 4, 5 or 6 intramuscular injection points, at a total dose of 50 U to 150 U and in a total volume of 0.15 to 0.35 ml.

11. The method of claim 10, wherein the botulinum neurotoxin is used in the treatment of moderate or severe glabellar frown lines or severe glabellar frown lines, based on investigator ratings using the Facial Wrinkle Scale (FWS) at maximum frown, and wherein the botulinum toxin is injected (i) at a total dose of 70 U to 130 U and in a total volume of 0.15 ml to 0.35 ml or (ii) at a total dose of 80 U to 120 U and in a total volume of 0.15 ml to 0.25 ml.

12. The method of claim 1, wherein the botulinum toxin is administered at an interval of 6 to 9 months between two consecutive treatment sessions.

* * * * *